United States Patent
Hammiche et al.

(10) Patent No.: US 6,200,022 B1
(45) Date of Patent: Mar. 13, 2001

(54) METHOD AND APPARATUS FOR LOCALIZED DYNAMIC MECHANO-THERMAL ANALYSIS WITH SCANNING PROBE MICROSCOPY

(75) Inventors: Azzedine Hammiche, Lancaster; Hubert Murray Montague-Pollock, Carnforth; Michael Reading, Milton Keynes, all of (GB)

(73) Assignee: TA Instruments, Inc., New Castle, DE (US)

( * ) Notice: Subject to any disclaimer, the term of this patent is extended or adjusted under 35 U.S.C. 154(b) by 0 days.

(21) Appl. No.: 09/224,600

(22) Filed: Dec. 31, 1998

Related U.S. Application Data

(63) Continuation-in-part of application No. 08/837,547, filed on Apr. 21, 1997, now Pat. No. 6,095,679, and a continuation-in-part of application No. 09/178,849, filed on Oct. 26, 1998, now Pat. No. 6,030,383.
(60) Provisional application No. 60/070,142, filed on Dec. 31, 1997.

(51) Int. Cl.[7] ............................. G01N 25/20; G01N 25/18
(52) U.S. Cl. .................................. 374/46; 374/43; 374/20
(58) Field of Search ........................ 374/43, 46, 166, 374/124, 33, 31, 110, 164, 11, 44, 5, 20; 73/105; 250/306, 234

(56) References Cited

U.S. PATENT DOCUMENTS

| | | | |
|---|---|---|---|
| 5,224,775 | 7/1993 | Reading et al. ........................ | 374/11 |
| 5,248,199 | 9/1993 | Reading ................................. | 374/11 |
| 5,441,343 | 8/1995 | Pylkki et al. ......................... | 374/137 |
| 5,463,897 | * 11/1995 | Prater et al. ............................ | 73/105 |
| 5,467,642 | * 11/1995 | Hosaka et al. ......................... | 73/105 |
| 5,471,064 | * 11/1995 | Koyanagi et al. ................. | 250/452.2 |
| 5,515,719 | * 5/1996 | Lindsay ................................. | 73/105 |
| 5,619,035 | * 4/1997 | Weiss et al. .......................... | 250/306 |
| 5,641,897 | * 6/1997 | Schuman ............................... | 73/105 |
| 5,661,235 | * 8/1997 | Bonin .................................... | 73/105 |
| 5,825,020 | * 10/1998 | Hansma et al. ....................... | 73/105 |
| 5,831,181 | * 11/1998 | Majumdar et al. .................... | 73/105 |
| 5,874,668 | * 2/1999 | Xu et al. ............................... | 73/105 |
| 5,877,497 | * 3/1999 | Binnig et al. ........................ | 250/306 |
| 5,877,891 | * 3/1999 | Park et al. ............................ | 359/372 |
| 5,929,438 | * 7/1999 | Suzuki et al. ......................... | 374/164 |
| 5,936,237 | * 8/1999 | Van Der Weide .................... | 250/234 |
| 5,939,719 | * 8/1999 | Park et al. ............................ | 250/306 |
| 5,990,477 | * 11/1999 | Tomita ................................. | 250/306 |
| 6,006,594 | * 12/1999 | Karrai et al. .......................... | 73/105 |

OTHER PUBLICATIONS

Localizedd Thermal Analysis Using Minitaurized Restive Probe, A. Hammiche, M. Reading, H.M. Pollock, M. Song, and D.J. Hourston, *Review of Science Instruments* 67 4268–4278 (Dec. 1996).
*Atomic Force Microscopy with Forced Modulation Imaging:*, P. Maivald, H.J. Butt, S.A.C. Gould, C.B. Prater., B. Drake, J.A. Gourley, V.B. Elings, and P.K. Hansma, *Nanotechnology*, vol. 2 p. 103 (1991).

(List continued on next page.)

*Primary Examiner*—G. Bradley Bennett
*Assistant Examiner*—Gail Verbilsky
(74) *Attorney, Agent, or Firm*—Shaw Pittman

(57) ABSTRACT

A system and method for performing localized mechano-thermal analysis with scanning probe microscopy ("MASM") is disclosed. In a preferred embodiment an image of the surface or subsurface of a sample is created. A localized region of the sample is selected from the image. Using a scanning microscope, an active or passive thermal probe is positioned at the selected region. A temperature ramp is applied to the localized region. In addition, a dynamic or modulated stress or strain is applied to the localized region. Force data resulting from the applied temperature and stress or strain is collected and processed to produce a graph or fingerprint of the dynamic mechanical and/or calorimetric properties of the selected localized region.

20 Claims, 11 Drawing Sheets

OTHER PUBLICATIONS

P.E. Mazeran and J.L. Loubet in *Tribiology Letters*, vol. 3, p. 125 (1997).

N.A. Burnham, A.J. Kulik, G. Germaud, P.J. Gallo and F. Oulevey, *Journal of Vacuum Science and Technology*, vol. B14, p. 764–799 (1996).

N.A. Burnham, A.J. Kulik, G. Germaud, P.J. Gallo and F. Oulevey, *Journal of Vacuum Science and Technology*, vol. B14, p. 1308–1392 (1996).

F. Oulevey, G. Gremaud, A. Semoroz, A.J., Kulik, N.Aa. Burnham, E. Dupas, and G. Gourdon, *Review of Scientific Instruments*, vol. 69 p. 2085–2094 (1998).

J.M.R. Weaver, L.M. Walpita, and H.K. Wickramasinghe, *Nature*, vol. 342, p. 732 (1989).

E.L. Florin, M. Radmacher, B. Fleck, and H.E. Gaub in *Review of Scientific Instruments*, vol. 65, p. 639 (1994).

\* cited by examiner

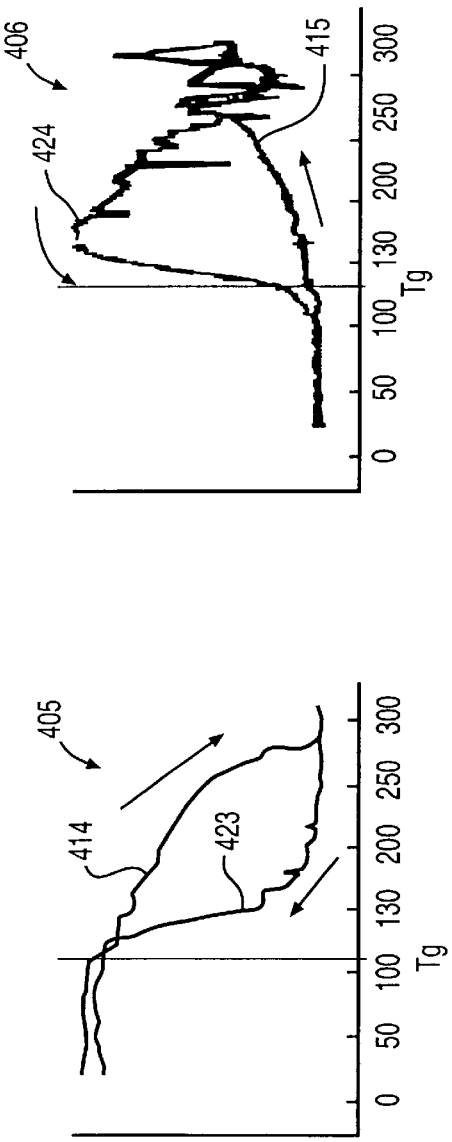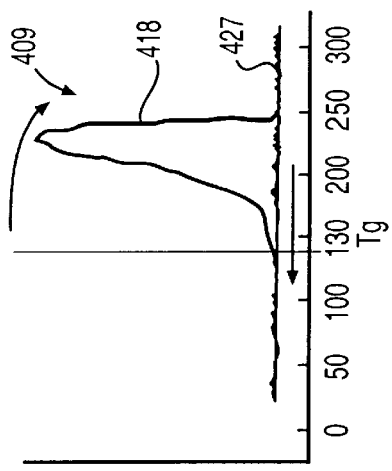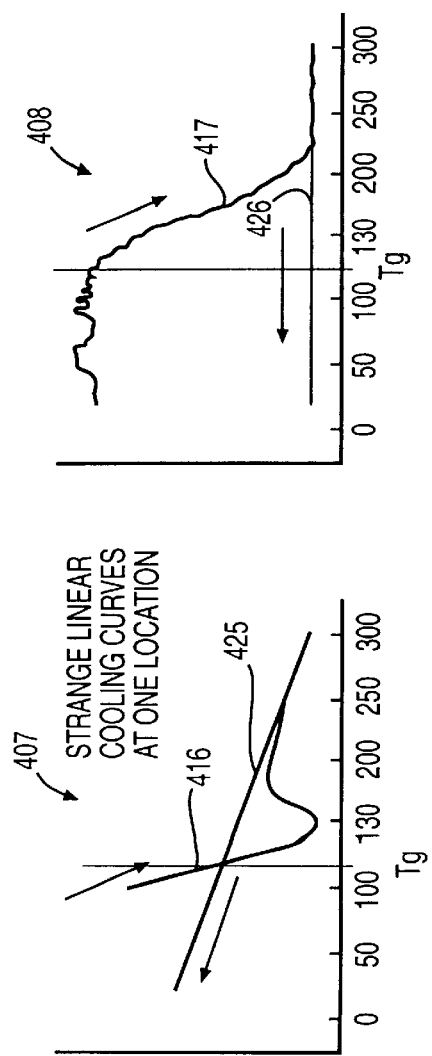

METHOD AND APPARATUS FOR LOCALIZED DYNAMIC MECHANO-THERMAL ANALYSIS WITH SCANNING PROBE MICROSCOPY

CROSS-REFERENCE TO RELATED APPLICATIONS

The present application is a continuation-in-part of U.S. patent application Ser. No. 08/837,547, filed on Apr. 21, 1997 now U.S. Pat. No. 6,095,679 (the "'547 application" or the "parent '547 application"), which is incorporated by reference herein in its entirety, and a continuation-in-part of U.S. patent application Ser. No. 09/178,849, filed on Oct. 26, 1998 now U.S. Pat. No. 6,030,383 (the "'849 application"), which is incorporated by reference herein in its entirety, and further claims priority from the filing date of U.S. Provisional Application No. 60/070,142, filed on Dec. 31, 1997.

BACKGROUND OF THE INVENTION

1. Field of the Invention

The present invention relates generally to thermal analysis methods and apparatus. More specifically, the present invention relates to static and dynamic thermomechanical analysis of localized regions of inhomogeneous samples that are identified and selected at high spatial resolution using scanning probe microscopy.

2. Description of the Related Art

Techniques for the thermomechanical characterization of solids and thin films are well-known and widely used. A description of such methods is given in "Thermal Analysis—Techniques and Applications" by E. L. Charsley and S. B. Warrington (eds.), Royal Society of chemistry, Cambridge, England (1992), which is hereby incorporated by reference in its entirety herein. There are several problems with these methods.

One problem is a practical one. Conventional thermomechanical or dynamic mechanical analysis experiments are often very time consuming, typically requiring several hours to complete. Consequently, solutions to urgent problems in industry are often delayed.

Another problem is related to sampling or data collection. Frequently, the sample being analyzed is either too small or too thin, or it is buried within a larger component from which it is difficult or impossible to extract. For example, the problems associated with obtaining a sufficient sample of a thin film that is firmly adhered to a substrate or sandwiched between two other layers are well-known.

Another problem is more fundamental in nature. Thermal methods are particularly useful in studying the morphology of polymer and polymer-containing samples. Modulated Temperature Differential Scanning Calorimetry (MTDSC), which was developed several years ago by Reading and co-workers, has greatly increased the quality of the structural information that can be obtained by calorimetry. See, M. Reading in Trends in Polymer Science vol. 1 pp. 248–53 (1993) and U.S. Pat. No. 5,224,775 to Reading et al. (the "'775 patent"), both of which are hereby incorporated by reference in their entirety herein. One advantage of MTDSC is that 'reversing' and 'non-reversing' processes can be separated. A second advantage of MTDSC is the improvement in the sensitivity and resolution with which glass transitions can be measured. As a result, scientists have found that MTDSC offers unique benefits in the study of curing systems, semi-crystalline polymers, and, in particular, polymer blends and related systems. But, even this advanced method cannot give spatially resolved information.

Moreover conventional thermomechanical analysis is performed using bulk samples, and consequently does not provide spatially resolved data. The inability of conventional thermal analytical techniques to give spatially resolved information is a critical shortcoming because modern polymeric materials are usually blends or composites with complex morphologies whose evaluation is crucial to the determination of their material properties. But, conventional thermal analysis techniques provide no information regarding the size of the domains or how they are distributed in space.

Therefore, it would be advantageous to use the advantages offered by each of the techniques described above and others described below by incorporating them into a technique for localized thermomechanical and calorimetric analysis, together with high-resolution microscopy.

SUMMARY OF THE INVENTION

The present invention is a thermal analysis system and method which allows a user to obtain images whose contrast is determined by either surface topography, or by subsurface variations in mechanical or thermal properties, using an active or passive thermal probe. In general, thermal analysis is a set of techniques including differential scanning calorimetry ("DSC"), modulated temperature differential scanning calorimetry ("MTDSC" or "MDSC®"), dynamic mechanical analysis ("DMA"), thermomechanical anslysis ("TMA"), thermogravimetric analysis ("TGA") and differential thermal analysis ("DTA").

In a preferred embodiment of the present invention, a region of the sample is selected for analysis from an image of the sample. This region is subjected to a localized temperature heating or cooling ramp. The heat is supplied by the thermal probe itself, or by a similar adjacent probe, with or without the addition of supplementary general heating as provided by a sample heater stage. Several kinds of measurements are made during application of the temperature ramp. One measurement is a measurement of quasi-static and dynamic mechanical compliance of the selected region. Another measurement is a measurement of the heat flow into the sample. These measurements can be used to generate graphs or fingerprints of the localized region of the sample under study. Thus, the present invention provides localized thermomechanical and calorimetric analysis measurements simultaneously.

The present technique for performing localized thermomechanical analysis is termed Mechanothermal Analysis with Scanning Microscopy ("MASM"). Two MASM techniques are disclosed. "Static MASM" localizes conventional thermomechanical analysis ("TMA"), i.e., studies involving the application of zero frequency (linear) temperature programs to the sample being analyzed. Static MASM is described in F. Oulevey, A. Hammiche, H. M. Pollock, N. A. Burnham, M. Song, D. J. Hourston and M. Reading, "Phase transitions in polymers: towards dynamic mechanical analysis with submicron spatial resolution," in "Surfaces and interfaces of polymers and composites," European Physical Society Conference on Molecular Physics, vol. 21B, Lausanne, Jun. 1–6 1997, R. Pick and G. Thomas, eds., European Physical Society 1997, pp. 155–56, which is hereby incorporated by reference in its entirety.

"Dynamic MASM" localizes Dynamic Mechanical Analysis ("DMA"). In DMA, a sinusoidal stress or strain is imposed on a sample to be analyzed. Any stress or strain which can be characterized as a function of one or more frequencies and amplitudes can be used. The resulting data is generally displayed in curves representing the storage modulus and the loss modulus as a function of temperature. Thermal events are derived from the storage and loss modulus data. Although, DMA does not reveal all the information provided by differential scanning calorimetry, it is several orders of magnitude more sensitive for the study of some phase transitions and relaxation spectra. For such events, therefore, MASM offers a higher sensitivity than calorimetric analysis with scanning microcscopy ("CASM"), as described, for example, in the '547 application.

A first object of the present invention is to use a scanning probe microscope to obtain images from which regions may be selected for the subsequent acquisition of localized thermomechanical data.

Another object of the present invention is to subject a localized region of a sample to both upward and downward temperature ramps, and at the same time to impose a combination of fixed and sinusoidally-modulated strain, while measuring the resultant force.

Another object of the present invention is to subject a localized region of a sample to both upward and downward temperature ramps, while simultaneously imposing a combination of fixed and sinusoidally-modulated force on the region, and then measuring the resultant strain.

Another object of the present invention is to use data resulting from the localized applied stress or strain in the presence of upward and downward temperature ramps to detect meltings, glass transitions and other thermal events, and to distinguish between reversible and irreversible contributions to the phenomena revealed in such events.

Another object of the present invention is to provide an ability to collect both MASM and CASM data substantially simultaneously.

Another object of the present invention is to select individual regions of a sample surface with a spatial resolution of a few tens of nanometers, on which to perform localized thermomechanical measurements.

Another object of the present invention is to obtain scanning probe microscopy images whose contrast is determined by, and thus reveals, the spatial variations in thermomechanical properties over the surface of an inhomogeneous sample.

These and other objects of the present invention are described in greater detail in the detailed description of the invention, the appended drawings and the attached claims.

DESCRIPTION OF THE FIGURES

FIGS. 4A–4I illustrate graphically the glass transition obtained from analyzing polystyrene using Dynamic MASM according to a preferred embodiment of the present invention.

DETAILED DESCRIPTION OF THE INVENTION

Figure 1:
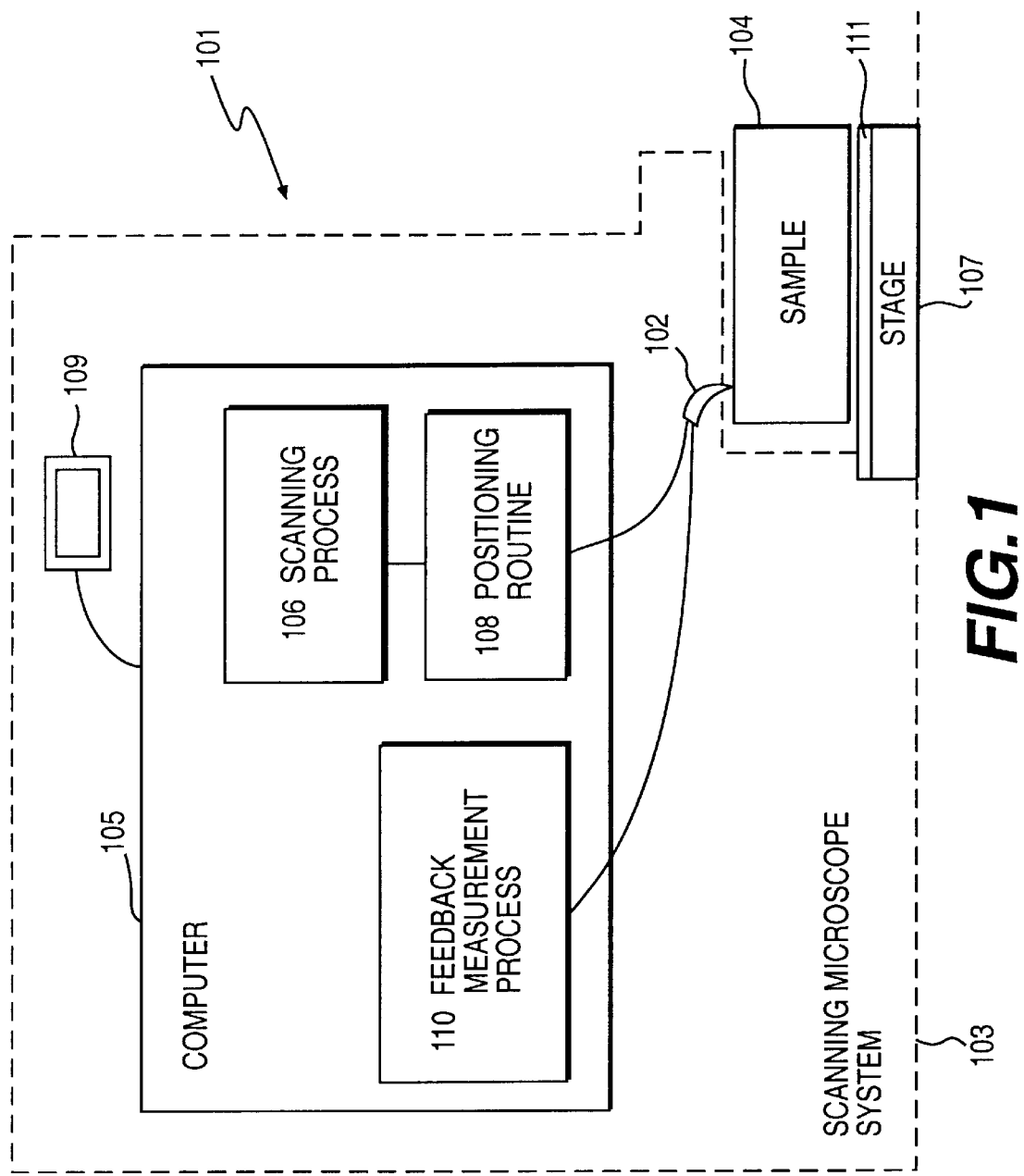
FIG. 1 illustrates schematically a MASM system according to a preferred embodiment of the present invention, using a scanning thermal microscope.

A brief description of some aspects of the '547 application and other related technologies will aid in understanding the present invention. As described in the '547 application, information regarding the size and distribution of domains must be obtained using microscopy techniques. Until the system described in the '547 application, however, conventional forms of sub-micron microscopy could show structure but could not easily reveal the chemical composition of the features observed for organic materials under ambient conditions. For this reason, the interpretation of microscopic images was often uncertain especially in complex 'real life' systems that typically consist of many components.

This problem was solved using a novel form of Scanning Probe Microscopy ("SPM"), known as Calorimetric Analysis with Scanning Microscopy ("CASM"), which is described in the parent '547 application. CASM uses a fine-scale thermal probe that enables thermal analysis to be carried out on a microscopic scale. CASM combines spatially resolved thermal information with a very rapid form of thermal analysis that can overcome many of the sampling problems mentioned above.

Most conventional methods of microscopy employ an energy beam that emerges from a small source and spreads out according to the rules of diffraction. The extent of this spreading is normally governed by the wavelength associated with the energy flux. However, if the sample is within the "near-field" region, i.e., significantly less than one wavelength away from the source, then a greatly reduced beam diameter can be achieved.

In scanning thermal microscopy techniques, including CASM and MASM, the interaction between the probe and the sample is confined within a region of space that is not much larger than the size of the source itself. In general, this probe/sample interaction can involve force, heat, magnetic or any other manner in which the probe and sample affect one another. This principle is applied in all conventional SPM techniques, in which a sharp probe is brought into close proximity to the surface of a sample causing some probe/sample interaction to occur. This interaction is monitored as the probe is scanned over the surface. An image is then computer-generated. The image contrast represents variations of some property (e.g., physical, mechanical, chemical) of the sample across the scanned area.

One such apparatus for scanning probe microscopy is the Atomic Force Microscope ("AFM"). In conventional AFM, the height of a very sharp probe above the surface being scanned is controlled by a feedback system. The feedback system keeps the force between the probe and the surface of the sample constant. The probe height is monitored, and provides the data that is used to create image contrast which represents the topography of the scanned area. AFM can achieve very high, even atomic, resolution.

R. B. Dinwiddie, R. J. Pylkki and P. E. West in "Thermal Conductivity Contrast Imaging with a Scanning Thermal Microscope," Thermal Conductivity 22, T. W. Tsong (ed.) (1994) describe a specialized Afm probe which also acts as a thermal probe to both detect temperature and act as a heat source. This probe is also described in U.S. Pat. No. 5,441, 343 to Pylkki et al. (the "'343 patent"). As descrbied in the '547 application, this probe is used with a scanning microscope in which the contact force of the probe is maintained at a constant level as the probe is scanned across the surface of the sample.

As described in the '343 patent and the '547 application, the probe is an elongated loop of Wollaston wire, shaped in the form of a cantilever whose end forms the resistive element. The resistance of that element varies with temperature. Alternately, the probe's temperature can be set by passing a current of appropriate value through it. As in conventional AFM, a mirror is attached across the loop which allows the contact force of the element on the sample to be held constant, while the probe is scanned across the surface of the sample as in conventional atomic force microscopy.

In operation, the probe is used as a highly localized heat source by passing a current through it. Its temperature can be set constant or time varying. As the probe is brought close to the surface of a sample, heat flows from the probe to the sample. The amount of heat flowing varies according to various properties of the sample at the location under the probe. This varying heat flow causes the temperature of the resistive element to change which changes its resistance. A feedback circuit is preferably used to sense the change in the probe resistance (due to the temperature change) and adjusts the amount of current flowing through the probe to force it back to its original resistance value (and therefore its set temperature). In the preferred embodiment described in the '547 application, a differential signal is then monitored, either directly or through a lock-in amplifier. The differential signal is used to either (1) to produce localized analysis plots of amplitude and phase data versus temperature that provide calorimetric information at a specific position on the sample, or (2) to construct an image whose contrasts represent variations in thermal conductivity and/or diffusivity across a scanned area. In the latter case, the time-varying current through the resistive elements generates thermal waves in the sample.

In CASM, the sample probe, attached to a scanning probe microscope, is positioned at a desired location on the surface within the field of view. Localized calorimetry is then performed at that position by inducing and detecting local phase transitions. This is achieved by ramping the temperature of the probe by passing an appropriate current through it. To that temperature ramp a small temperature oscillation is superimposed by adding a modulated current into the probe. Apparatus for performing CASM is described in the '547 application and in A. Hammiche, M. Reading, H. M. Pollock, M. Song and D. J. Hourston, "Localized thermal analysis using a miniaturized resistive probe," Rev. Sci. Instrum. vol. 67 pp. 4268–4274 (1996), which is incorporated by reference in its entirety herein.

CASM thus enables determination of thermal properties of materials using a miniaturized resistive thermal probe by performing localized thermal analysis experiments to obtain calorimetric information from volumes of materials of the order of a few cubic microns, as opposed to the few cubic millimeter volumes of material required in conventional bulk calorimetry.

In one application of CASM, SPM in its thermal form is combined with calorimetry in its MTDSC form to implement a new analytical technique which achieves highly localized calorimetry. This technique has been described in U.S. Pat. No. 5,248,199 to Reading et al (the "'199 patent"), which is incorporated be reference herein in its entirety, and in the '547 application It has also been described in the following publications: A Hammiche, H. M. Pollock, M. Song and D. J. Hourston, Measurement Science and Technology 7, p.142–150 (1996); A. Hammiche, H. M. Pollock, D. J. Hourston, M. Reading and M. Song, J. Vac. Sci. Technol., vol. B14, p. 1486–91 (1996); A. Hammiche, M. Reading, H. M. Pollock, M. Song and D. J. Hourston, Rev. Sci. Instrum., vol. 67, p.4268 (1996); and H. M. Pollock, A. Hammiche, M. Song, D. J. Hourston and M. Reading in Journal of Adhesion, vol. 67, pp.217–34 (1998).

For example, the MTDSC technique described above that has been conventionally used to perform bulk thermal analysis experiments of a sample material, can be used in microscopy using two highly miniaturized resistive probes, in a differential arrangement. Suitable probes include those developed by Topometrix Corporation as described above with reference to the '343 patent.

As a method for spatially-resolved thermal analysis, CASM itself has two limitations. First, CASM yields no data on mechanical properties and how they change as the sample undergoes a thermal transition. Second, the spatial resolution is limited by the finite size of the thermal probe, which is in some cases inadequate. A higher spatial resolution, together with information on the sample's mechanical properties, is given by another type of SPM, which includes several different variants. These have been given different names, for example, scanning viscoelastic microscopy and scanning local-acceleration microscopy, but may all be grouped under the general heading of "Atomic Force Microscopy with Force Modulation Imaging." They do not in themselves provide a means of thermal analysis, but a brief description is provided to aid in understanding some aspects of the present invention.

In Atomic Force Microscopy with Force Modulation Imaging ("AFM-FMI"), the image contrast is determined by spatial variation in mechanical properties such as elastic modulus. This is achieved by means of a sinusoidal modulation of the force between probe and sample (either directly, or through a modulation of the position of either the probe or the sample). The details of this force modulation imaging mode are described by P. Maivald, H. J. Butt, S. A. C. Gould, C. B. Prater, B. Drake, J. A. Gurley, V. B. Elings and P. K. Hansma in Nanotechnology, vol. 2, p. 103 (1991). Thus, viscoelastic properties, for example, can be studied with a submicron lateral resolution as reviewed by T. Kajiyama, K. Tanaka, S. R. Ge and A Takahara in Progress in Surface Science, vol. 52, pp. 1–52 (1996). P. E. Mazeran and J. L. Loubet in Tribology Letters, vol. 3, p. 125 (1997) show that unless the amplitude of the modulation is kept very small, of the order of a few nanometers or less, variations in probe/sample friction rather than mechanical properties may dominate the image contrast.

N. A. Burnham, A. J. Kulik, G. Gremaud, P. J. Gallo and F. Oulevey in Journal of Vacuum Science and Technology, vol. B14, p. 794–99 (1996) have shown that this undesirable affect can be avoided if the sample's surface is vibrated at a very high frequency (approaching the megahertz range), just above the resonance of the tip-sample system. In this case, the inertia of the tip prevents it from completely following the imposed displacement, so that the sample is elastically deformed. Contact stiffness (related to elasticity of the sample) is obtained from the residual displacement of the tip, at a spatial resolution of better than 40 nm resolution for samples ranging from compliant polymers to stiff ceramics. This is described by N. A. Burnham, G. Gremaud, A. J. Kulik, P. J. Gallo and F. Oulevey in Journal of Vacuum Science and Technology, vol. B14, pp. 1308–92 (1996), which is hereby incorporated by reference herein in its entirety. This form of AFM-FMI has been combined with a sample heating stage, as described by F. Oulevey, G. Gremaud, A. Semoroz, A. J. Kulik, N. A. Burnham, E. Dupas and G. Gourdon, Review of Scientific Instruments, vol. 69, pp. 2085–94 (1998), in order to combine non-localized thermomechanical analysis with scanning microscopy.

In one aspect of the present invention, the inventors have discovered how to combine CASM, whish provides a localized temperature ramp and hence localized MTDSC with microscopy at micron-level spatial resolution with AFM-FMI, which provides local information on mechanical properties and spatial resolution at the nanometer scale, but does not provide localized thermomechanical analysis.

In addition to analyzing the surface of a sample under study, the subsurface of a sample can be profiled and imaged using thermal waves. This can be done by modulating the temperature of the probe to generate evanescent thermal waves in a material under study to thereby generate subsurface images. The modulation frequency of the time-varying current is functionally related to the depth below the surface of the sample at which an image of the sample is desired. As described in Almond, et al., "Photothermal Science and Techniques," p. 15, Chapman and Hall (London 1996), which is hereby incorporated by reference in its entirety, the penetration depth is proportional to the square root of the thermal diffusivity of the sample divided by the frequency of the applied temperature wave.

By scanning over the surface of the sample, contrast can be developed corresponding to particular locations on the sample to create an image of the thermal properties of the sample at the particular locations. A sub-surface image is thus generated. The depth of material below the sample surface that is contributing to the image can be controlled by suitably choosing the temperature modulation frequency. Subsurface imaging in this manner is described in the '547 application.

FIG. 1 illustrates schematically a MASM system 101 according to a preferred embodiment of the present invention. MASM system 101 uses a scanning microscope system 103 to derive localized mechanothermal information and/or calorimetric information about the sample being analyzed. Referring to FIG. 1, a thermal probe 102 interacts with a sample 104 to determine characteristics of sample 104. Such characteristics include mechanothermal and calorimetric properties of sample 104.

Probe 102 is part of a scanning microscope system 103. Preferably, scanning microscope system 103 is an atomic force microscope such as described in the '199 patent and the '547 application. Atomic force microscopes are also referred to as scanning force microscopes Preferably scanning microscope system 103 includes a stage 107 on which sample 104 rests when it is being analyzed. In a preferred embodiment, stage 107 is a heater stage to provide an optional generalized, i.e., bulk heating, to sample 104. Probe 102 is operatively coupled to a computer 105 through a piezoelectric actuator (shown in FIG. 7 and described below), which can rasterize probe 102 across the surface of sample 104. The piezoelectric actuator can impart a mechanical modulation or vibration on probe 102 to cause probe 102 to provide the localized stress or strain required for performing localized dynamic mechanical analysis according to a preferred embodiment of the present invention. Computer 105 is preferably a component of scanning microscope system 103. Computer 105 can be any general purpose computer which can execute computer programs to perform the functions described below. Such computers are well-known and need not be described further.

A number of software processes (computer programs) execute on computer 105. Three of these pertinent to the preferred embodiment of the present invention are an atomic force microscope scanning routine 106, a positioning routine 108 and a feedback measurement routine 110.

Figure 6:
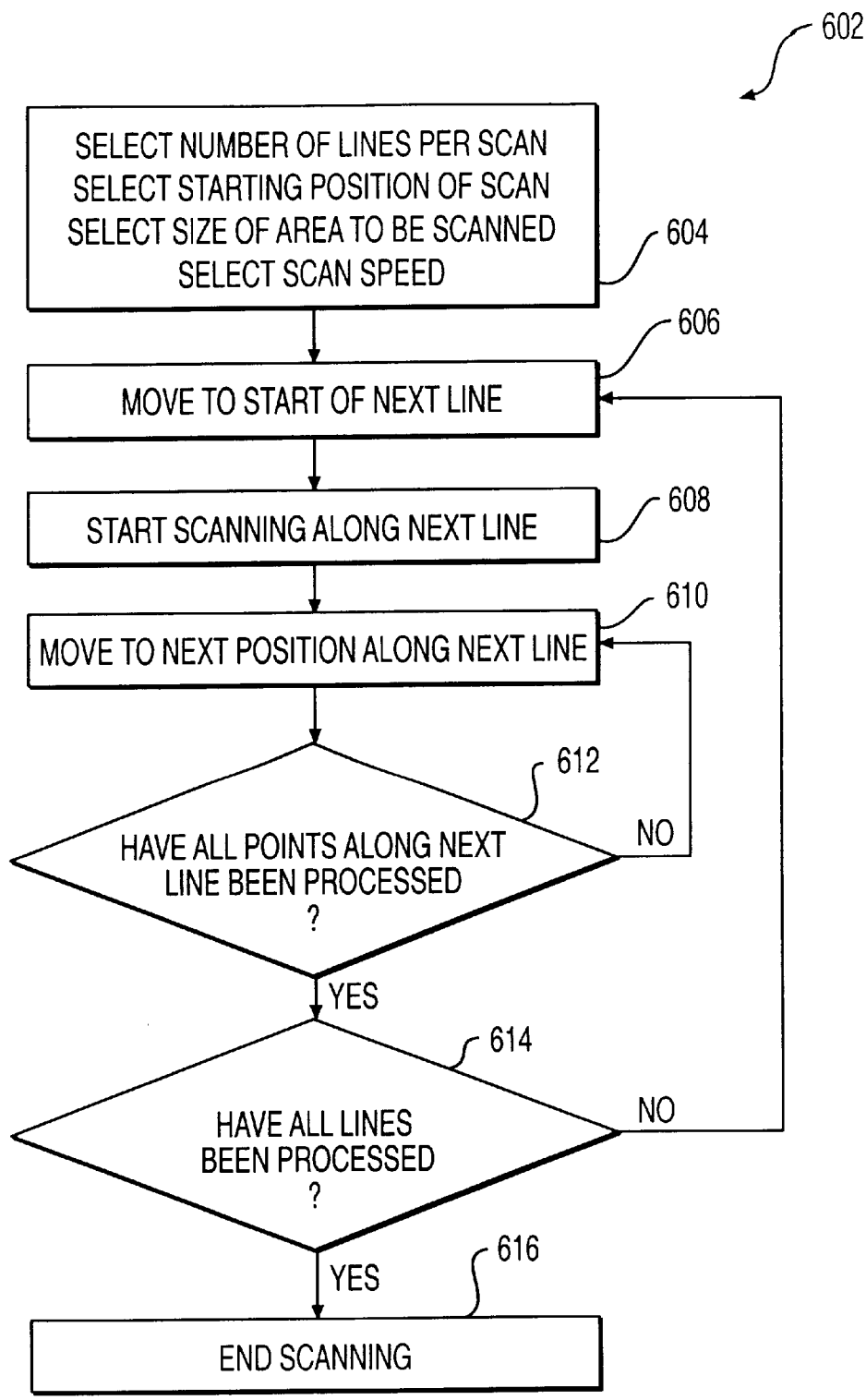
FIG. 6 is a flow chart representing a scanning routine for controling scanning of the scanning thermal microscope according to a preferred embodiment of the present invention.

Scanning routine 106 controls the scanning of the surface of sample 104 by controlling rasterizing of probe 102 across the surface of sample 104. Referring to FIG. 6, scanning routine 106 is described using flow chart 602. The scanning routine begins in step 604 where the number of lines per scan, the starting position of the scan, the size of the area to be scanned and the scan speed are selected. This selection can be performed either automatically or manually by an operator. Scanning routine 106 continues in step 606 where the probe is placed at the start of the next line to be rastered. The next line is the first line at the beginning of the scanning process. Scanning routine 106 continues in step 608 by starting to scan along the next line at the first position. Then in step 610, scanning routine 106 causes the scan to continue at the next position along the next line. At this point, scanning process determines in step 612 whether all points along the next line have been scanned. If they have not, scanning process 106 continues in step 610 by moving to the next point along the next line. If all of the points along the next line have been scanned, scanning process 106 determines whether all of the lines in the raster have been processed. If they have not, scanning process 106 continues in step 606 by positioning probe 102 at the start of the next line to be scanned. If all of the lines in the raster have been processed, scanning process 106 continues in step 616 by ending the scanning. The scanning process is described in the parent '547 application.

Positioning routine 108 controls the position of probe 102 on the surface of sample 104. Positioning routine 108 and scanning routine 106 work with each other to control position to develop surface and/or sub-surface images of sample 104 as described in the parent '547 application. When an area has been scanned, data recorded during the scan is used by computer 105 to generate an image whose contrast represents variations of some properties of sample 104 across the scanned area. Preferably, the image is displayed on a video display device 109 connected to computer 105.

Using a computer mouse or other selection device in a conventional manner, a cursor can be placed anywhere on the displayed image. Preferably, a desired position is chosen by depressing a mouse button when the cursor is positioned on the area of interest. This activates positioning routine 108, which moves probe 102 to the desired position, on the surface of sample 104. Localized analysis is then performed at this position.

In the preferred embodiment, feedback measurement routine 110 is a force/feedback measurement routine. Feedback routine 110 operates to maintain a substantially constant force of the probe on the surface of sample 104. In the preferred embodiment, where an atomic force microscope is used, feedback measurement routine 110 is automatically achieved by continuously monitoring the bending of the cantilever-shaped probe as it is scanned across the surface of the sample. A constant bending—and therefore constant force—is maintained by the piezoelectric transducer, or actuator, to which probe 102 is attached. Distortion of the transducer is achieved by having appropriate voltages applied to it so that the tip of the probe is made to follow the topography of the scanned area at a constant force. Feedback measurement routine 110 is described in the parent '547 application.

Thermal probe 102 can be either an active thermal probe or a passive thermal probe. In the preferred embodiment, the active thermal probe is either a thermally-imaging thermal probe or a high-resolution thermal probe. The active thermally-imaging type of probe consists either of a Wollaston-type of resistive probe as described in the '343 patent, or of the high-resolution batch-fabricated type made by lithography as described by H. Zhou, A. Midha, G. Mills, S. Thoms, S. K. Murad and J. M. R. Weaver, "Generic scanned-probe microscope sensing by combining micromachining and electron beam lithography," Journal of Vacuum Science and Technology, vol. B16, pp. 54–58 (1998) ("Zhou et al), or by a variety of other methods. In the preferred embodiment, the high-resolution type probe described by Zhou et al is modified by adding a sharp, hard object of small size and high thermal conductivity attached to its extremity. The generic technique described by Zhou et al is used to manufacture a probe whose extremity is hard and of high thermal conductivity, and shaped such that contact with the sample occurs over a very small area. Thus, each type of active thermal probe has a sharp thermally conductive tip, so that high spatial resolution to be achieved.

The passive thermal probe is preferably a thermocouple, or sharp AFM probe, for measurements at highest spatial resolution. Alternative methods for probe heating include a modulated laser light beam. Examples of passive thermal probes suitable for use in the present invention are described in J. M. R. Weaver, L. M. Walpita, and H. K. Wickramasinghe, Nature, vol. 342, p. 732 (1989); C. C. Williams and H. K. Wickramasinghe, Soc. Photographic Instrumentation Engineers, vol. 897, p. 129 (1988) and E. Oesterschulze, M. Stopka and R. Kassing, Microelectronic Engineering, vol. 24, 107 (1994).

Where a passive probe is used, an electrical heater can be placed elsewhere on the tip of the probe to provide heat for local thermal analysis and imaging. Also, the expansion and contraction caused by modulated heating can be used to impart stress or strain modulation on the tip of the probe, which in turn imparts a modulated stress or strain to the sample at the selected localized region.

The hardware and software to sense and to control the probe temperature, and to position the probe in the preferred embodiment is described in the parent '547 application. Briefly, when operated at constant temperature (spatial scanning) mode, the probe is heated by passing a current through it. A constant temperature of the probe is maintained by maintaining its resistance constant as it is scanned across regions of different thermal properties. This is achieved automatically by adjusting the current flowing through the probe. Alternatively, the temperature of the probe can be modulated by adding a modulating current component. In this case, two additional thermal signals can be recorded—an amplitude and a phase signal—by monitoring the AC voltage across the probe at the fundamental and harmonic frequencies of the modulated current. In a preferred embodiment this is accomplished using a lock-in amplifier ("LIA") as described below and in the parent '547 application. In operation, MASM system 101 preferably is used to first obtain one or more images of sample 104. The images can be either surface or sub-surface images. From these images, a region is selected for acquisition of localized thermomechanical data. In addition, localized calorimetry can be performed on the selected region.

When a sub-surface image is desired, the depth below the surface contributing to image contrast in scanning thermal microscopy may be controlled through the use of temperature modulation. The temperature modulation can be applied using either an active type of thermal probe or the high-resolution batch-fabricated type of thermal probe. Alternatively a sharp AFM probe or a passive thermal probe such as a thermocouple, heated externally by means of a modulated laser beam or other heat source, may be used. An example of such other heat source is a resistive heater located elsewhere on the probe. The depth of the image is proportional to the square root of the ratio of thermal diffusivity to modulation frequency.

In a first preferred embodiment, a thermally-imaging probe is used to acquire sub-surface images. Thus, the microscope acts as a scanning thermal microscope giving multiple surface and sub-surface images of the sample, such that the image contrast corresponds to variations in either thermal diffusivity, surface topography or chemical composition.

Using probe 102, MASM system 101 can also subject a localized region of sample 104 to both upward and downward temperature ramps. Substantially simultaneously, MASM system 101 imposes a combination of fixed and sinusoidally-modulated strain or stress on the localized region of sample 104. MASM system 201 measures the resultant force or strain. Other modulations including square wave, triangle wave, sawtooth wave and combinations of these can be used. In the preferred embodiment of the present invention, the stress or strain applied to the localized region of sample 104 under test is determined by measuring the deflection of the laser beam which monitors the bending of the probe structure. The measured probe bending is applied to a mathematical model of the thermo-mechanical interaction between probe and the sample to provide a quantitative estimate of the stress and strain that the probe applied to the region of the sample under test. Alternatively, the measured probe bending can be graphed to determine physical properties of the selected region of the sample. The graphs can be stored as a fingerprint for comparison with the results of analyses on different samples.

Figure 7A:
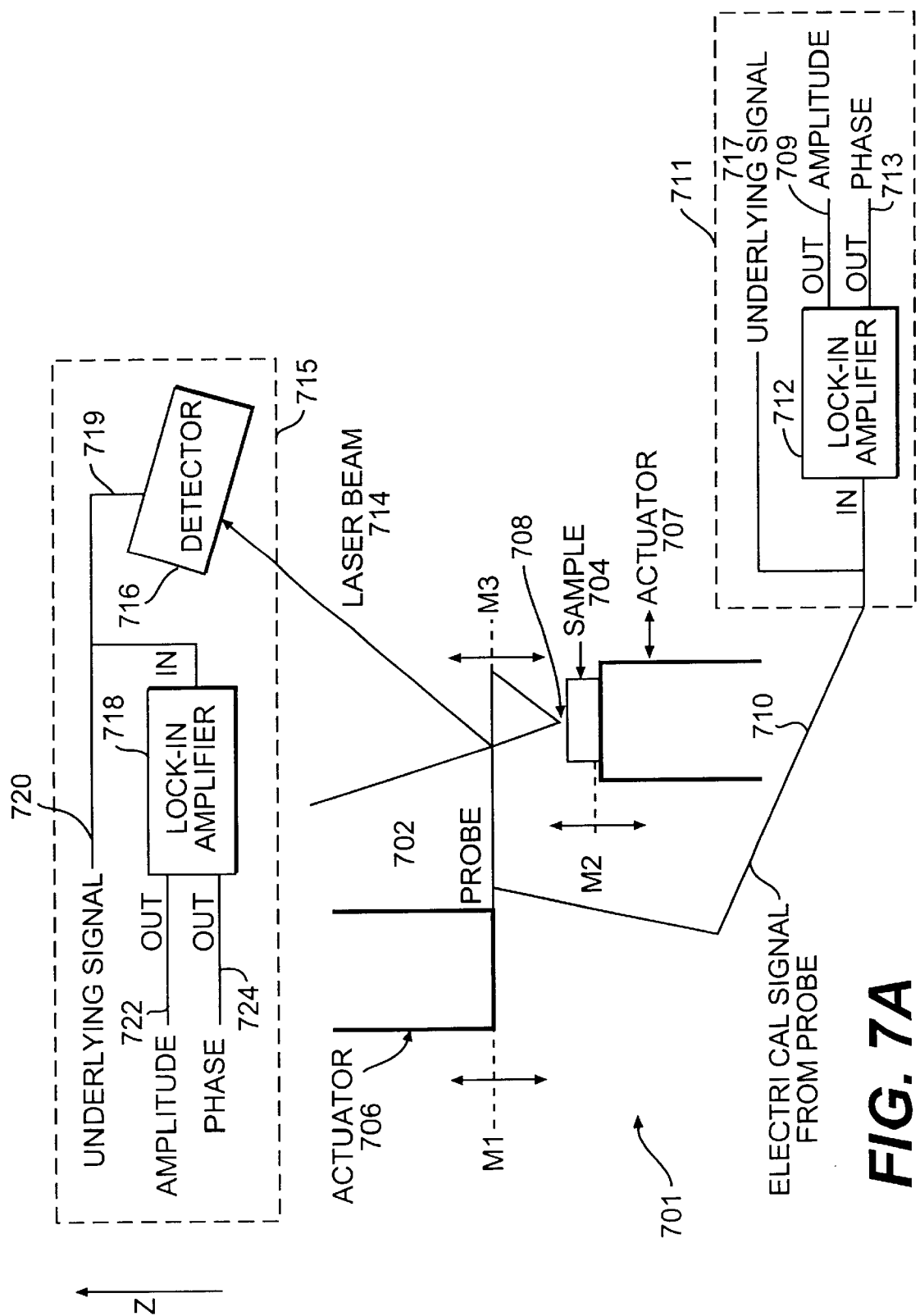
FIG. 7A is a schematic illustrating application of localized dynamic stresses and strains and temperatures according to a preferred embodiment of the present invention.
Figure 7C:
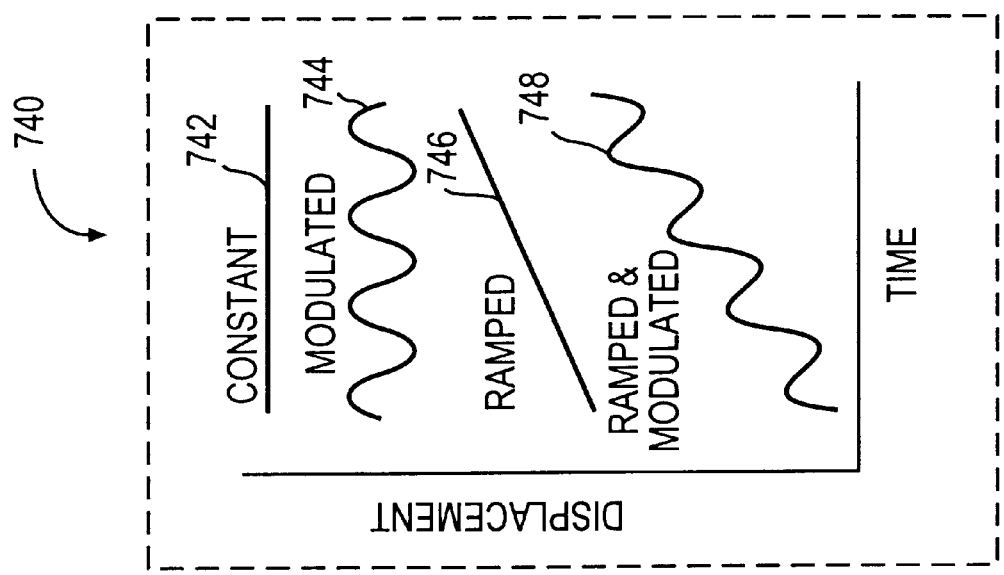
FIG. 7C is a graphical representation of the types of temperature profiles which can be imparted to the apex of the probe for localized heating according to a preferred embodiment of the present invention.
Figure 7B:
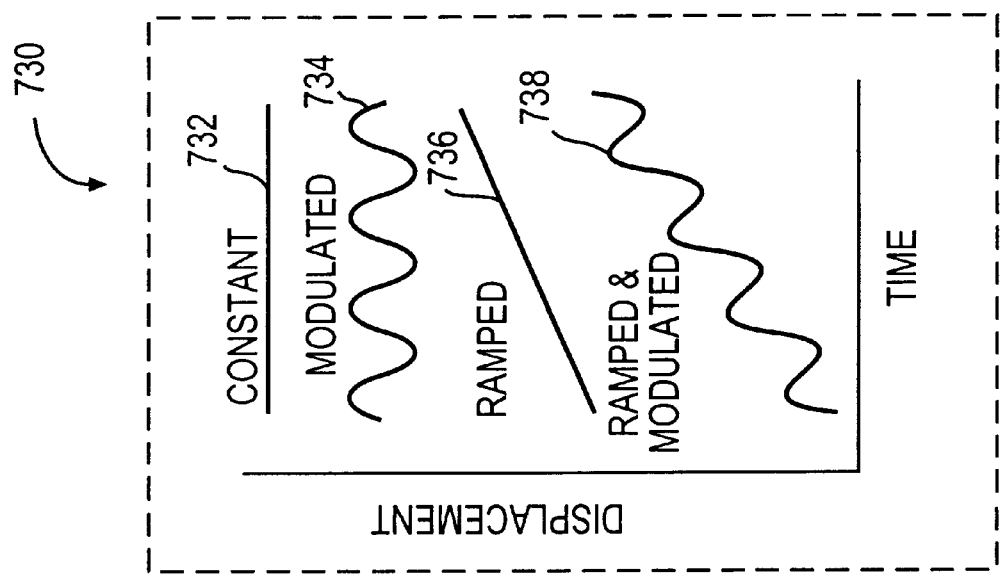
FIG. 7B is a graphical representation of the types of displacements which can be imparted on the probe or sample to produce localized stress or strain according to a preferred embodiment of the present invention.

Referring to FIGS. 7A–7C, the generation and acquisition of localized dynamic data is described. FIG. 7A illustrates schematically a probe 702 attached to an actuator 706. Actuator 706 imparts motion to probe 702. Preferably actuator 706 is a piezoelectric transducer. Probe 702 interacts with a sample 704. Sample 704 can be placed on an actuator 707. Actuator 707 imparts motion to sample 704. Preferably actuator 707 is a piezoelectric transducer. Actuator 707 can also include a heater to provide general heating to sample 704.

To generate and acquire localized dynamic data the position of either sample 704 or probe 702 is modulated. Preferably, the modulation is sinusoidal. However, any modulation can be used, including triangle modulation, sawtooth modulation, square wave modulation and any combination of thereof. The tip is placed on a point selected as described above. Then, a controlled force is applied to it.

FIG. 7B illustrates graphically examples of forces that can be applied to the selected localized region according to a preferred embodiment of the present invention. These forces include a constant force 732, a modulated force 734, a ramped force 736 and a modulated ramped force 736.

There are several embodiments for applying the desired force when performing dynamic MASM as described herein. In one embodiment, the temperature of probe 702 is ramped while it is in contact with sample 704. The position of the extremity of piezoelectric transducer 706, onto which the probe 702 is attached, is mechanically modulated along the vertical dimension as shown by arrow M1, using one of the force profiles illustrated in FIG. 7B. In the preferred embodiment, the modulated bending of the probe is detected using a laser beam deflection technique. A laser beam 714 is reflected off of a reflective surface, of probe 702. The reflective surface can be a mirror attached to probe 702. The laser beam is reflected to a laser beam processor 715. Laser beam processor 715 includes a detector 716 which detects laser beam 714 and converts it to an electrical signal 719.

Electrical signal 719 represents the interaction between probe 702 and sample 704 in the presence of the applied force and temperature. The probe/sample interaction involves several aspects. First, there is an underlying force, which is determined by the strength of the force between the apex of the tip and the sample. Second, there is a modulated force interaction caused by an imposed mechanical modulation of either (1) the vertical sample position with respect to the frame of the laboratory, (2) the extremity of the vertical transducer, onto which the probe is attached, with respect to the frame of the laboratory, or (3) the vertical probe tip position with respect to the frame of the laboratory, as described above.

Electrical signal 719 is input to a lock-in amplifier ("LIA") 718 tuned to the fundamental frequency of the modulation and its harmonics. LIA 718 outputs a amplitude signal 722 and phase signal 724, corresponding to the amplitude and phase contributions of the modulation at the fundamental frequency and its harmonics. Laser beam processor 715 also outputs the contribution to electrical signal 719 of the underlying modulation ramp as underlying signal 720. The amplitude signal 722, phase signal 724 and underlying signal 720 are input to a modeling algorithm which quantitatively estimates the localized stress and strain. Alternatively, the amplitude signal 722, phase signal 724 and/or underlying signal 720 can be graphed to determine physical properties of the selected region of the sample. The graphs can be stored as a fingerprint for comparison with the results of analyses on different samples.

Alternatively, the modulated bending of probe 702 is determined electrically. The modulated bending of probe 702 generates electrical signal 710. Electric signal 710 is input an elecrical signal processor 711. Electrical signal processor 711 includes to a lock-in amplifier ("LIA") 712 tuned to the fundamental frequency of the modulation and its harmonics. Electrical signal 710 is input to LIA 712. LIA 712 outputs a amplitude signal 709 and phase signal 713, corresponding to the amplitude and phase contributions of the modulation at the fundamental frequency. Electrical signal processor 711 also outputs the contribution to electrical signal 710 of the underlying modulation ramp as underlying signal 717. The amplitude signal 709, phase signal 713 and underlying signal 717 are input to a modeling algorithm which quantitatively estimates the localized stress and strain. Alternatively, the amplitude signal 709, phase signal 713 and/or underlying signal 717 can be graphed to determine physical properties of the selected region of the sample. The graphs can be stored as a fingerprint for comparison with the results of analyses on different samples.

In another embodiment for perfoming dynamic MASM, the temperature of probe 702 is ramped while it is in contact with sample 704. The position of the tip of the probe is mechanically modulated along the vertical dimension using for example, an electromagnetic technique, as illustrated by arrow M3 using one of the force profiles illustrated in FIG. 7B. In the preferred embodiment the modulated bending of the probe is detected using a laser beam deflection technique as described above. Alternatively, an electrical technique can be used to determine the modulated bending of probe 702 as described above.

In another embodiment for performing dynamic MASM, the temperature of probe 702 is ramped while it is in contact with sample 704. The position of sample 704 is mechanically modulated along the vertical direction using actuator 707. Preferably actuator 707 is a piezoelectric transducer, though any apparatus for controllably moving sample 704 can be used. In the preferred embodiment the modulated bending of the probe is detected using a laser beam deflection technique as described above. Alternatively, an electrical technique can be used to determine the modulated bending of probe 702 as described above.

In another embodiment for performing dynamic MASM, the temperature of probe 702 is ramped while it is in contact with sample 704. At the same time, the temperature of the probe is modulated by adding a modulated current through it. FIG. 7C illustrates graphically examples of temperatures that can be applied to the selected localized region according to a preferred embodiment of the present invention. These temperatures include a constant temperature 742, a modulated temperature 744, a ramped temperature 746 and a modulated ramped temperature 746. In the preferred embodiment the modulated bending of the probe is detected using a laser beam deflection technique as described above. Alternatively, an electrical technique can be used to determine the modulated bending of probe 702 as described above.

Alternatively, magnetic modulation is applied directly to probe 102. Magnetic modulation of probe 102 to control the force with which it interacts with the surface of sample 104 is described in E. L. Florin, M. Radmacher, B. Fleck and H. E. Gaub in Review of Scientific Instruments, vol. 65, p.639 (1994). Alternatively, the movement of the probe's tip exansion and contraction resulting from a modulated temperature program can be used to provide the desired stress and strain to the localized region of sample 104.

Alternatively, the temperature of probe 702 is ramped while it is in contact with sample 704. Local thermal expansion of sample 704 occurs at the selected region. This local thermal expansion is measured by probe 702. Depending on the spring constant of probe 702 and the stiffness of sample 704, the force between sample 704 and probe 702 increases, in addition to the increase in height and temperature of sample 704. Results from this embodiment are descrbied later with respect to FIG. 2.

The transducer for imposing sinusoidal vibrations is as described, for example, in F. Oulevey, G. Gremaud, A. Semoroz, A. J. Kulik, N. A. Burnham, E. Dupas and D. Gourdon, Review of Scientific Instruments, vol. 69, pp. 2085–94 (1998). In a preferred embodiment, a transducer 111 is incorporated in or attached to stage 107. Alternatively, sample 104 rests on a transducer 111 without a stage 107. The transducer mechanically modulates the position of the sample with respect to the frame of the laboratory.

As the temperature increases the sample often softens and the probe indents further into the sample. Force measurement system 110, which is preferably provided as part of the atomic force microscope 103, is used to record the force between probe and sample continuously during this measurement. Force feedback system 103 provided by the atomic force microscopy apparatus 103 can be switched off during this measurement. The heat flow of sample 104 can be measured substantially simultaneously. In this manner MASM and CASM data are acquired substantially simultaneously.

MASM system 101 can further be used to select individual regions of a sample surface with a spatial resolution of a few tens of nanometers, or better, on which to perform the thermomechanical measurements described above. Preferably, probe 102 is a high-resolution probe where the heater, whether electrical, optical (laser), or some other heating technique, is not located at the apex of the tip. Depending on which of the above-described types of high-resolution probe is used, the thermal time constant of the probe can be too long for modulated-temperature thermal images or CASM scans to be obtained. But, enough heat is still transmitted from probe to sample to achieve the temperature ramp needed for MASM measurements. As a result, the spatial resolution of the MASM measurements can be much improved.

MASM 101 can also be used to obtain scanning probe images whose contrast is determined by the spatial variations in thermomechanical properties over the surface of an inhomogeneous sample. Using these images, studies of the variation in thermomechanical properties as a function of the position on (or in) the sample can be performed.

To perform such studies, it is sometimes necessary to reduce the time required to raise each individual region to the required temperature, while the probe is scanning the sample 104 spatially. In the preferred embodiment, this is accomplished by using a sample stage 107 that is heated. Use of a heated sample stage allows the entire sample 104 to be raised to a temperature that is slightly below the particular thermal transition whose presence is taken as an indication of the presence of a particular chemical phase. Having so heated sample 104, only a small quantity of localized heat from the thermal probe is then needed to cycle each region in turn through the transition. Consequently, the total time required for a measurement is substantially reduced. That is, the time for any localized region's measurement, as well as the time for measurement of the entire sample 104 is substantially reduced.

In a preferred embodiment using a heater or temperature stage, the sample, through action of the heater stage, is maintained at a temperature just below the transition of interest. With the tip of the probe at the same, or slightly above the, temperature of the heater stage, but still below the temperature range of the transition of interest, the sample's thermomechanical properties are imaged using one of the imaging techniques described above. The temperature of the probe's tip is then raised above or substantially within the temperature range of the transition of interest and the imaging is repeated in the same region. In this second image, the thermomechanical properties of those regions which undergo the transition of interest should change substantially. By comparing the two images, the location of the regions that undergo the transition should be revealed. These region can be made clearer by well-known image processing techniques. For example, the two images can be subtracted from one another. The resulting image should put the regions of interest in sharp relief.

In another preferred embodiment using the heater stage, a long period, i.e. low frequency, temperature modulation which traverses the whole or part of the temperature range of a transition of interest, is selected. This is accompanied by using a higher frequency temperature modulation. For example, the temperature modulation frequency is five times that of the long period and has ⅕th of its amplitude. The amplitude or phase of the high frequency modulation will be itself modulated at the frequency of the longer period oscillation in regions containing the phase that undergoes the transition in the temperature range of the long period modulation. A Fourier transform of either the phase or the amplitude of the response to the high frequency modulation will thus provide, at the frequency of the long period, a signal related to the presence of the selected transition and, therefore, corresponding phase. As the tip is rastered over the surface of the sample this signal will map the spatial distribution of the phase of interest. This mode can be used with or without a hot stage set at a temperature a little below the onset temperature of the selected transition. This mode can be applied to the calorimetric or thermomechanical signals generated by CASM or Dynamic MASM.

The MASM systems described above can be used to detect meltings, glass transitions and other thermal events, and to distinguish between reversible and irreversible contributions to the phenomena revealed in such events. An example of the detection of a glass transition is shown in FIGS. 2 and 3, and of a melting in FIG. 4.

Figure 2:
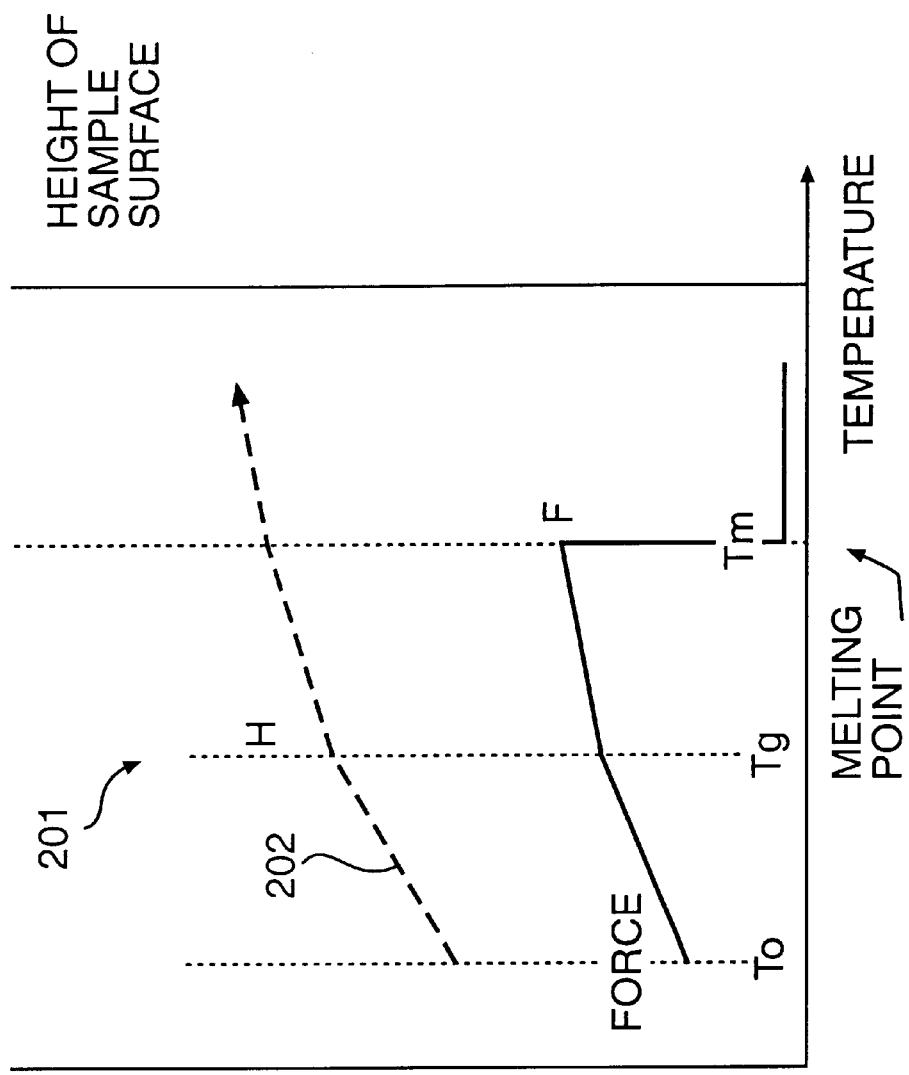
FIG. 2 illustrates graphically data obtained from a MASM experiment according to a preferred embodiment of the present invention using an AFM.
Figure 3A:
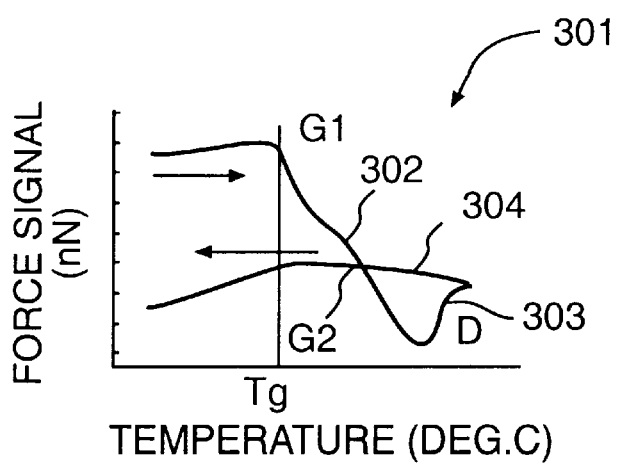
FIGS. 3A–3F illustrate graphically data obtained from analyzing polystyrene using static MASM according to a preferred embodiment of the present invention.
Figure 3B:
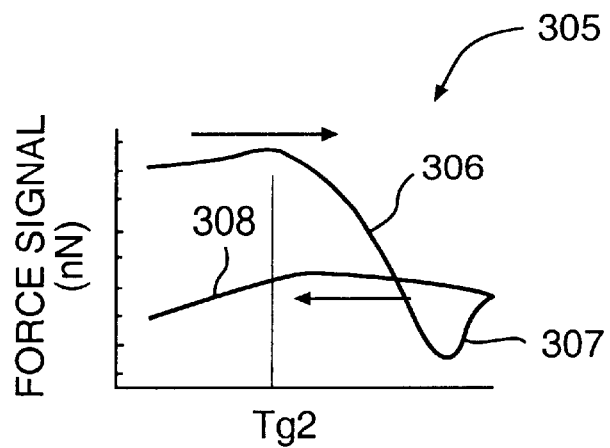
Figure 3C:
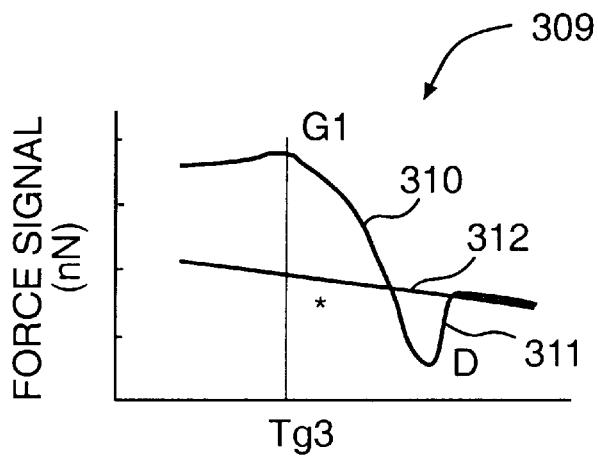
Figure 3D:
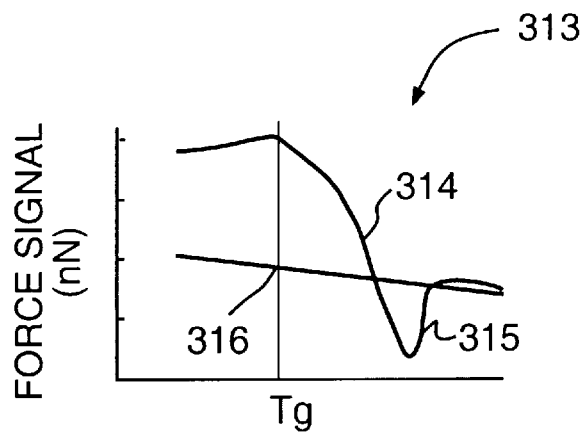
Figure 3E:
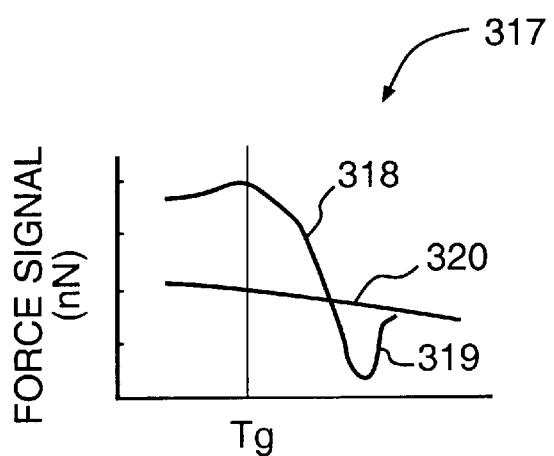
Figure 3F:
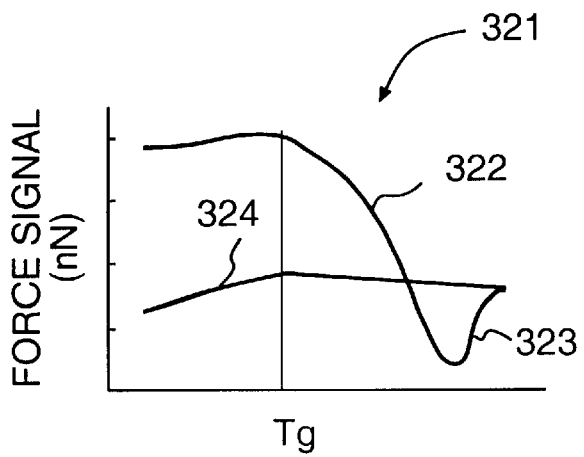
Figure 4B:
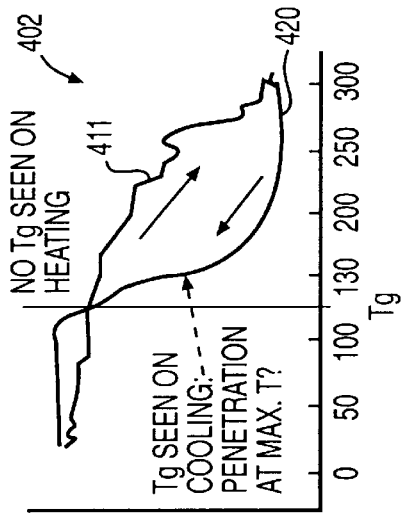
Figure 4D:
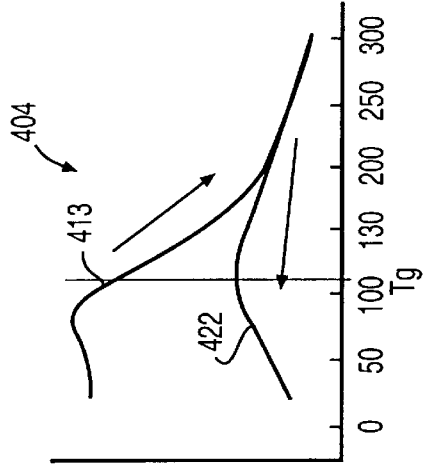
Figure 4A:
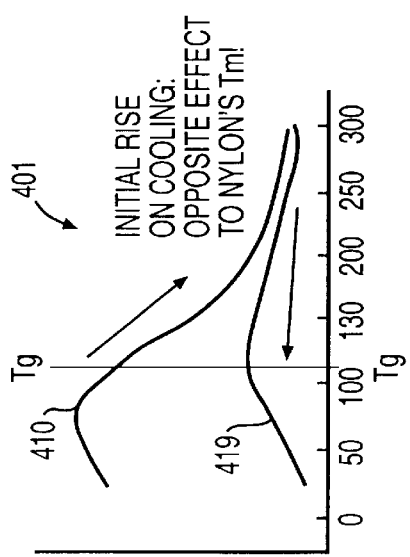
Figure 4C:
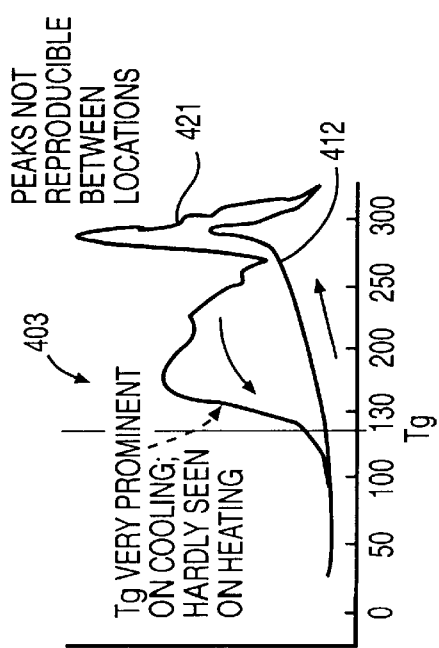
Figure 5A:
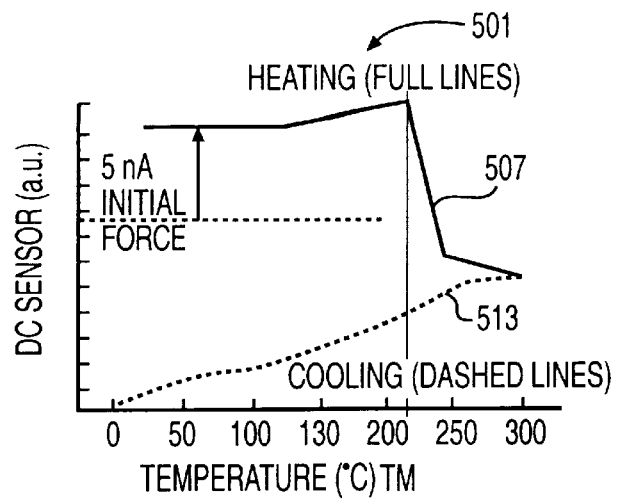
FIGS. 5A–5F illustrate graphically the melting transition obtained from analyzing nylon using Dynamic MASM according to a preferred embodiment of the present invention.
Figure 5B:
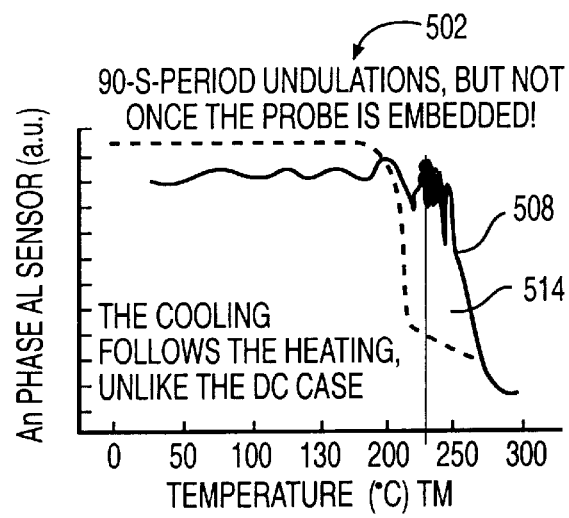
Figure 5C:
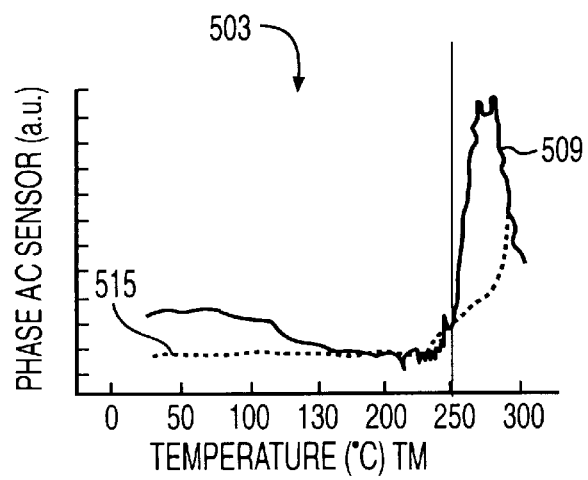
Figure 5D:
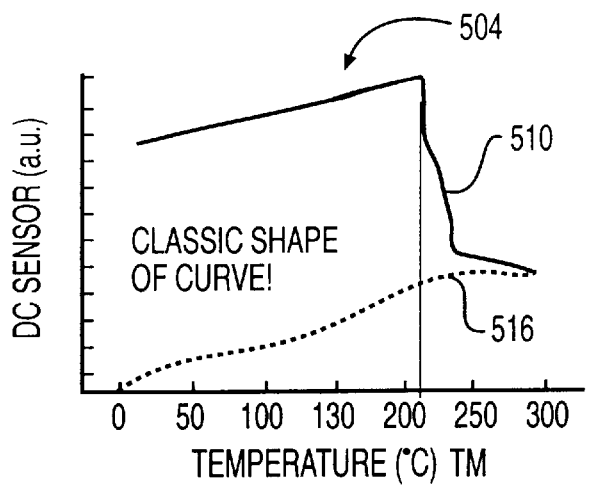
Figure 5E:
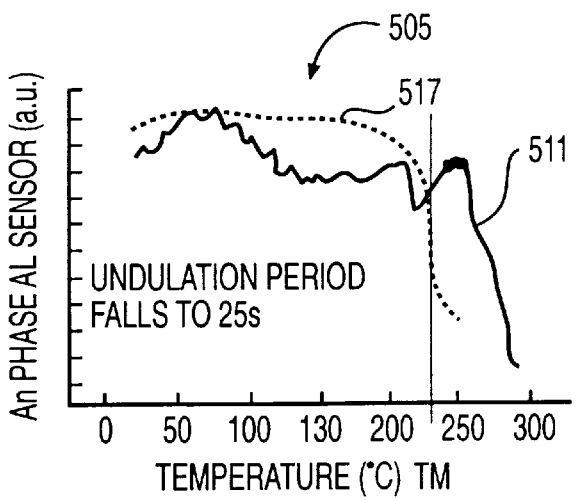
Figure 5F:
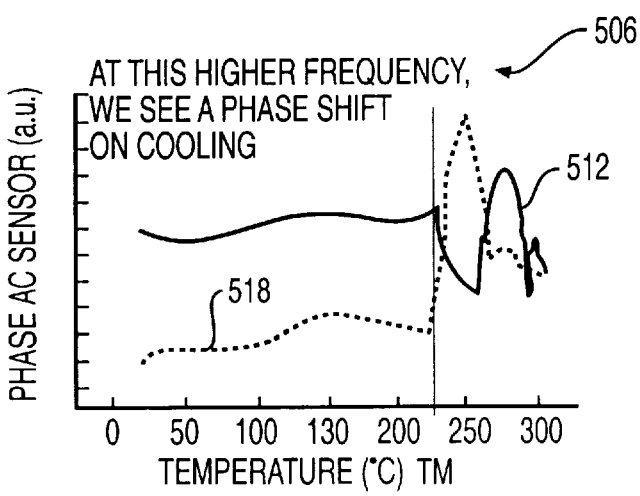

Referring to FIG. 2, an example of data derived by MASM 101 using an AFM is illustrated by graph 201. The curves shown in graph 201 were generated using static MASM, in which there is no mechanical vibration imposed on the sample or probe.

Graph 201 shows two curves: a probe height curve 202, labeled "H," and a force curve 204, labeled "F." Both curves are plotted as functions of temperature beginning at temperature $T_0$. Curve 202 represents the height of the probe at a particular location on the surface of the sample. The increase in height shown in curve 202 is caused by thermal expansion of the sample as it heats. Curve 204 represents that force exerted by the surface of the sample on the probe.

As can be seen from graph 201, both curves 202 and 204 change when the glass transition temperature $T_g$ is reached. Of further interest, is that the force curve 204 drops to a very low value when the sample melts upon reaching its melting temperature, $T_m$.

FIGS. 3A–3F illustrate in graphs 301, 305, 309, 313, 317 and 321, the results of performing static MASM experiments at six different locations on a sample of polystyrene. In each experiment, the polystyrene sample was exposed first to an upward (heating) temperature ramp, having a substantially constant heating rate through a range of temperatures from approximately 25 degrees Celsius to 300 degrees Celsius, and then to downward (cooling) temperature ramp, having a substantially constant cooling rate through a range of temperatures from approximately 300 degrees Celsius to 25 degrees Celsius. The probe can be scanned, in temperature, from approximately room temperature to approximately 600 degrees Celsius. However, if the sample is attached to a cooling stage, for example, a liquid nitrogen cooled stage or a Peltier cooling cascade stage, the temperature range can be extended below room temperature.

Graphs 301, 305, 309, 313, 317 and 321 show the force signal resulting from conventional DMA data processing performed at different locations in the sample. Curves 302, 306, 310, 314, 318 and 322 result from the application of the heating ramp, and curves 304, 308, 312, 316, 320 and 324 result from application of the cooling ramp.

The glass transition temperature (onset of liquidity) can be observed in each of heating curves data, curves 302, 306, 310, 314, 318 and 322, but in only curves 304, 308 and 324 of the cooling rate data. A possible explanation is that the maximum temperature was sufficient to degrade the polystyrene completely, so that the glass transition was not observed upon cooling. Alternatively, the glass transition is not detected on cooling because penetration has already occurred.

Another feature to note in each of the graphs is the rise 303, 307, 311, 315, 319 and 323 seen in each of the heating curves 302, 306, 310, 314, 318 and 322. The rises 303, 307, 311, 315, 319 and 323 may result from reversion to solid-like behavior which can result from degradation.

FIGS. 4A–4I illustrate in graphs 401–409, the results of performing dynamic MASM experiments at three different locations on a sample of polystyrene. Graphs 401–403 correspond to one location. Graphs 404–406 correspond to the second location. Graphs 407–409 correspond to the third location. In each experiment, the polystyrene sample was exposed to first a substantially constant heating ramp at approximately 25 degrees/minute through a range of approximately 25 degrees Celsius to 300 degrees Celsius, on which was superimposed a sinusoidal temperature modulation having a frequency of 20 hertz and an amplitude of 5 degrees Celsius, and then to a substantially constant (downward) cooling ramp at approximately 25 degrees/minute through a range of approximately 300 degrees Celsius to 25 degrees Celsius, on which was superimposed a sinusoidal temperature modulation having a frequency of 20 hertz and an amplitude of 5 degrees Celsius. The probe can be scanned, in temperature, from approximately room temperature to approximately 600 degrees Celsius. However, if the sample is attached to a cooling stage, for example, a liquid nitrogen cooled stage or a Peltier cooling cascade stage, the temperature range can be extended below room temperature. Curves 410–418 were produced from the applied heating ramps. Curves 419–427 were produced from the applied cooling ramps.

A lock-in amplifier was used to separate the contributions of the DC and AC components of the applied temperature program to the resulting data. Curves 401, 404 and 407 represent the contribution of the underlying heating and cooling ramps (upward and downward applied temperatures respectively) to the resulting data. Curves 402, 405 and 408 represent the amplitude or power of the AC component of the resulting data. The AC component is a product of the applied 20 Hz modulation. Curves 403, 406 and 409 represent the phase of the AC component of the resulting data.

The temperature of the glass transition for each location can be seen in each of the graphs as indicated by the temperature $T_g$. Some features to note are the substantially different response of the various location of the sample to similarly applied dynamic heating and cooling temperature profiles. In addition, interesting linear curves were observed in response to the applied cooling temperature ramp at the third location as illustrated by curves 425–427.

FIGS. 5A–5F illustrate in graphs 501–506, the results of performing dynamic MASM experiments to determine the melting temperature of nylon using two different modulation frequencies. In each of graphs 501–506, the force sensor signal from localized DMA apparatus according to a preferred embodiment of the present invention is plotted as a function of time for both applied heating and cooling temperature programs. Graphs 501–503 correspond to one vibration frequency (20 Hz). Graphs 504–606 correspond to a second vibration frequency (1 KHz). In both cases, the amplitude of vibration was approximately 1 micron.

In each experiment, the polystyrene sample was exposed to first a substantially constant heating ramp at approximately 25 degrees/minute through a range of approximately 25 degrees Celsius to 300 degrees Celsius, and then to a substantially constant (downward) cooling ramp at approximately 25 degrees/minute through a range of approximately 300 degrees Celsius to 25 degrees Celsius. The probe can be scanned, in temperature, from approximately room temperature to approximately 600 degrees Celsius. However, if the sample is attached to a cooling stage, for exmple, a liquid nitrogen cooled stage or a Peltier cooling cascade stage, the temperature range can be extended below room temperature. Curves 507–512 were produced from the applied heating ramps. Curves 513–518 were produced from the applied cooling ramps.

A lock-in amplifier was used to separate the contributions of the DC and AC components of the applied temperature program to the resulting data. Graphs 501 and 504 represent the contribution of the underlying heating and cooling ramps (upward and downward applied temperatures respectively) to the resulting data. Graphs 502 and 505 represent the amplitude or power of the AC component of the resulting data. The AC component is a product of the applied modulations. Graphs 503 and 506 represent the phase of the AC component of the resulting data.

The temperature where the nylon sample melts can be seen in each of the graphs as indicated by the temperature $T_m$.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A system for performing localized thermomechanical experiments on a sample, comprising:
    a scanning microscope;
    a computer coupled to said scanning microscope, said computer comprising;
        a video display device on which an image of the surface of the sample is displayed; and
        a selection device for selecting from the displayed image a localized region of the sample as a selected location;
    a thermal probe operatively coupled to said scanning microscope
    a probe positioning routine executing on said computer to cause said thermal probe to be positioned at the selected location; and
    wherein the thermal probe is heated or cooled while substantially simultaneously applying a mechanical stress or strain on the selected location, and measuring the force resulting from the applied stress or strain.

2. The system of claim 1, wherein said thermal probe is attached to an actuator operatively coupled to said scanning microscope, which actuator is moved to cause said thermal probe to impart said mechanical stress or strain.

3. The system of claim 1, wherein said sample rests on a stage, which stage is moved to cause said thermal probe to impart said mechanical stress or strain.

4. The system of claim 1, wherein said tip of said thermal probe is moved magnetically to impart said mechanical stress or strain.

5. The system of claim 1, wherein said heating causes said selected location to expand to cause a sample-probe interaction which imparts said mechanical stress or strain.

6. A method for performing localized thermomechanical experiments on a sample, comprising the steps of:

(a) creating an image of the surface or sub-surface of said sample;

(b) selecting a location of said sample from said image as a selected location;

(c) positioning a thermal probe at said selected region;

(d) heating said selected location;

(e) applying a mechanical stress or strain to said selected location; and (f) measuring a force resulting from said selected location.

7. The method of claim 6, wherein step (e) comprises the step of moving an actuator to which said thermal probe is attached to apply said mechanical stress or strain to said selected location.

8. The method of claim 6, wherein step (e) comprises the step of moving a stage on which said sample rests to apply said mechanical stress or strain to said selected location.

9. The method of claim 6, wherein step (e) comprises the step of magnetically moving said thermal probe to apply said mechanical stress or strain to said selected location.

10. The method of claim 6, wherein step (e) comprises the step of heating said selected region to thereby cause said selected location to expand to apply said mechanical stress or strain to said selected location.

11. A system for analyzing a sample, comprising:

a stage on which the sample to be analyzed is placed;

a display to show surface of the sample;

selection means to select a particular point on the surface of the sample to analyze using the display;

a probe to impart a localized mechanical stress or strain on the sample, and to locally heat the sample according to a temperature program to generate dynamic data regarding at least one surface property of the surface of the sample; and means for analyzing the dynamic data.

12. The system of claim 11, wherein the localized mechanical stress or strain can be characterized by a sinusoidal function.

13. The system of claim 11, wherein the localized mechanical stress can be characterized by the sum of a ramp function and a sinusoidal function.

14. The system of claim 11, wherein the temperature program can be characterized by a sinusoidal function.

15. The system of claim 11, wherein the temperature can be characterized by the sum of a ramp function and a sinusoidal function.

16. A method for analyzing a localized region of a surface of a sample comprising the steps of:

placing the sample on a stage of a microscope;

obtaining an image of the surface of the sample;

selecting a localized region of the surface of the sample for analysis;

placing a probe over the localized region;

applying a mechanical stress or strain and a temperature according to a temperature program to the localized region using the probe to generate dynamic data; and analyzing the dynamic data.

17. The method of claim 16, further comprising the step of applying a mechanical stress or strain that can be characterized by a sinusoidal function.

18. The method of claim 16, further comprising the step of applying a mechanical stress or strain that can be characterized by the sum of a ramp function and a sinusoidal function.

19. The method of claim 16, further comprising the step of applying a temperature program that can be characterized by a sinusoidal function.

20. The method of claim 16, further comprising the step of applying a temperature that can be characterized by the sum of a ramp function and a sinusoidal function.

* * * * *